United States Patent
Vogler et al.

(10) Patent No.: US 9,724,235 B2
(45) Date of Patent: Aug. 8, 2017

(54) LASER APPARATUS AND METHOD FOR LASER PROCESSING A TARGET MATERIAL

(71) Applicant: Novartis AG, Basel (CH)

(72) Inventors: Klaus Vogler, Eschenau (DE); Olaf Kittelmann, Berlin (DE)

(73) Assignee: Novartis AG (CH)

( * ) Notice: Subject to any disclaimer, the term of this patent is extended or adjusted under 35 U.S.C. 154(b) by 378 days.

(21) Appl. No.: 14/370,686

(22) PCT Filed: Feb. 27, 2013

(86) PCT No.: PCT/EP2013/053961
§ 371 (c)(1),
(2) Date: Jul. 3, 2014

(87) PCT Pub. No.: WO2014/131445
PCT Pub. Date: Sep. 4, 2014

(65) Prior Publication Data
US 2015/0230978 A1    Aug. 20, 2015

(51) Int. Cl.
*A61B 18/18*  (2006.01)
*A61F 9/008*  (2006.01)
*H01S 5/183*  (2006.01)
*H01S 5/14*   (2006.01)
*H01S 5/04*   (2006.01)

(52) U.S. Cl.
CPC ............. *A61F 9/008* (2013.01); *H01S 5/04* (2013.01); *H01S 5/146* (2013.01); *H01S 5/183* (2013.01)

(58) Field of Classification Search
CPC .. A61F 9/008; A61F 9/00802; A61F 9/00804; A61F 9/00825; A61F 9/0084; A61B 18/20; A61B 18/203; A61B 2018/2035; A61B 2018/2085; H01S 5/00; H01S 5/05; H01S 5/071; H01S 5/078; H01S 5/085
USPC ........ 606/3–6, 10–13, 17, 18; 372/39, 43.01
See application file for complete search history.

(56) References Cited

U.S. PATENT DOCUMENTS

| 6,735,234 B1 | 5/2004 | Paschotta et al. |
| 7,351,241 B2* | 4/2008 | Bendett ............... A61F 9/00827 128/898 |
| 8,982,916 B2* | 3/2015 | Zhang ..................... H01S 5/065 372/19 |
| 2002/0138069 A1* | 9/2002 | Peyman .................. A61F 2/145 606/5 |

(Continued)

FOREIGN PATENT DOCUMENTS

WO    2007092803 A2    8/2007

*Primary Examiner* — Ahmed Farah

(57) ABSTRACT

In an embodiment, a laser apparatus comprises a semiconductor laser, e.g., of the VECSEL type, for generating pulsed laser radiation having a pulse duration in the femtosecond range or shorter and having a pulse repetition rate of at least 100 MHz; a selector for selecting groups of pulses from the laser radiation, each pulse group comprising a plurality of pulses at the pulse repetition rate, wherein the pulse groups are time-displaced by at least 500 ns; a scanner device for scanning a focal point of the laser radiation; a controller for controlling the scanner device based on a control program including instructions that, when executed by the controller, bring about the creation of a LIOB-based photodisruption for each pulse group in a target material, e.g. human eye tissue.

16 Claims, 3 Drawing Sheets

(56) References Cited

U.S. PATENT DOCUMENTS

| | | | |
|---|---|---|---|
| 2003/0105456 A1* | 6/2003 | Lin | A61F 9/008 606/5 |
| 2004/0231682 A1* | 11/2004 | Stoltz | A61B 18/20 128/898 |
| 2008/0015662 A1 | 1/2008 | Tunnermann et al. | |
| 2010/0004643 A1 | 1/2010 | Frey et al. | |
| 2014/0288539 A1* | 9/2014 | Bischoff | A61F 9/00825 606/4 |
| 2016/0158061 A1* | 6/2016 | Foesel | A61F 9/0084 606/4 |

* cited by examiner

(12) United States Patent
US 9,724,235 B2

LASER APPARATUS AND METHOD FOR LASER PROCESSING A TARGET MATERIAL

CROSS REFERENCE TO RELATED APPLICATIONS

This application is a section 371 national stage phase of International Application No. PCT/EP2013/053961, filed 27 Feb. 2013, titled "LASER APPARATUS AND METHOD FOR LASER PROCESSING A TARGET MATERIAL," which is hereby incorporated by reference in its entirety.

The present disclosure is generally concerned with an apparatus and a method for laser processing a target material. More specifically, the apparatus and method of the present disclosure are aimed at a multi-pulse application of pulsed laser radiation to create microdisruptions in a target material.

A single-pulse application of pulsed laser radiation uses a single laser pulse to create a microdisruption in a target material. In contrast, a multi-pulse application creates a microdisruption in the target material through the combined effect of a plurality of radiation pulses applied successively at substantially the same location of the target material. Typically, each pulse of the plurality has insufficient energy and intensity to disrupt the material, but the aggregate effect of the pulse plurality achieves the desired disruption. In single-pulse applications, a focal point of the laser radiation is steered to a new position after each application of a pulse, wherein the locations of application of the pulses have little or no overlap. In multi-pulse applications, after a group of pulses is applied at substantially the same location of the target material the focal point of the laser radiation is moved to a new position for the application of a next group of pulses. While the pulses within a group have sufficient positional overlap to have the necessary aggregate effect for the achievement of the desired disruption of the material, the pulses of different groups have no or substantially no positional overlap.

Conventional single-pulse laser systems providing pulsed fs (femtosecond) laser radiation are equipped with a bulk or fiber laser oscillator and an amplifying device operating as a chirped pulse amplifier or a regenerative amplifier for amplifying the pulses. A pulse picker is employed to reduce the repetition rate of the pulses generated by the bulk or fiber laser oscillator to a value sufficiently low to allow for amplification of the pulses by the amplifying device. Other conventional designs of fs-laser systems employ a long-cavity or cavity-dump laser resonator to achieve the desired pulse energy needed for single-pulse applications on a target material.

EP 1 829 510 A1 discloses a fs-laser apparatus employing a double-pulse to achieve a photodisruption in human corneal tissue, wherein the double-pulse consists of a pre-pulse of lower energy and a main pulse of larger energy.

US 2003/0222324 A1 discloses a technique for the ablating removal of conductive links in an integrated circuit chip using sets of laser radiation pulses. Each pulse has insufficient energy to fully sever a link, but ablates a part of the link. Removal of the link material thus occurs in a step by step manner with each single pulse of the set.

In one aspect, the present disclosure provides a laser apparatus comprising: a laser source for generating pulsed laser radiation having an ultrashort pulse duration; a selector for selecting groups of pulses from the laser radiation, each pulse group comprising a plurality of pulses at a pulse repetition rate of at least 100 MHz, wherein the pulse groups have a group repetition rate of no more than about 1 MHz; a scanner device for scanning a focal point of the pulsed laser radiation; and a controller for controlling the scanner device based on a control program including instructions that, when executed by the controller, bring about the creation of a separation/disruption/damage in a target material.

In certain embodiments, the laser source includes a semiconductor laser. The semiconductor laser may be one of a VECSEL (vertical external-cavity surface-emitting laser) type, VCSEL (vertical-cavity surface-emitting laser) type and MIXSEL (modelocked integrated external-cavity surface-emitting laser) type.

In certain embodiments, the pulse repetition rate is at least 500 MHz, 800 MHz or 1 GHz.

In certain embodiments, a pulse group includes no less than 10 pulses or 20 pulses or 50 pulses or 80 pulses or 100 pulses.

In certain embodiments, a pulse group has a group duration of no more than 500 ns or 200 ns or 150 ns or 120 ns.

In certain embodiments, successive pulse groups are time-displaced by at least the duration of a pulse group.

In certain embodiments, at least one of the energy and peak power is nominally the same for all pulses of a group. Nominally refers to the setting of the laser apparatus emitting the pulses and means that the same energy and/or peak power target values apply for all pulses of a group. This does not preclude the occurrence of fluctuations of the actual energy or peak power values among the pulses of a group due to statistical processes.

In certain embodiments, the apparatus comprises an exit location for outputting the pulsed laser radiation towards a target material, wherein pulses output at the exit location are characterized by pulse characteristics ensuring the generation of a laser-induced optical breakdown in human eye tissue by each pulse group.

In certain embodiments, the aggregate energy of a group of pulses output at the exit location is in the range of nanojoules or microjoules. As a numerical and nonlimiting example, the aggregate energy of a group of pulses output at the exit location may be between 0.1 and 1 microjoules.

In certain embodiments, the energy of a single pulse within the pulse group output at the exit location is in the range of picojoules or nanojoules.

In certain embodiments, a first amplifier is provided for amplifying the pulses of the pulsed laser radiation prior to the selection of the pulse groups.

In certain embodiments, the first amplifier is configured for amplifying the energy of a pulse from picojoules to nanojoules.

In certain embodiments, a second amplifier amplifies the pulses selected by the selector.

In another aspect, the present disclosure provides a laser apparatus, comprising: a semiconductor laser (e.g. of the VECSEL, VCSEL or MIXSEL type) for generating pulsed laser radiation having a pulse duration in the femtosecond range or shorter and having a pulse repetition rate of at least 100 MHz; a selector for selecting groups of pulses from the laser radiation, each pulse group comprising a plurality of pulses at the pulse repetition rate, wherein the pulse groups are time-displaced by at least 500 ns; a scanner device for scanning a focal point of the laser radiation; and a controller for controlling the scanner device based on a control program including instructions that, when executed by the controller, bring about the creation of a LIOB-based photodisruption in a transparent target material (i.e. transparent to the radiation), e.g. human eye tissue, for each pulse group.

According to yet another aspect, the present disclosure provides a method of laser processing a target material, comprising: generating pulsed laser radiation having an ultrashort pulse duration using a VECSEL or other type of semiconductor laser; selecting groups of pulses from the laser radiation, each pulse group comprising a plurality of pulses at a pulse repetition rate of at least 100 MHz, wherein the pulse groups have a group repetition rate of no more than about 1 MHz; and steering a focal point of the pulsed laser radiation over a target area of a target material to create an incision in the target material.

In embodiments of the present disclosure, the target material is a biological material. In certain embodiments, the biological material is tissue of a human eye, for example, corneal tissue or human lens material. In other embodiments, the target material is a non-biological material or, in other words, an inanimate material.

Embodiments of the present disclosure will now be described by way of example in greater detail with reference to the attached drawings, in which.

Figure 1:
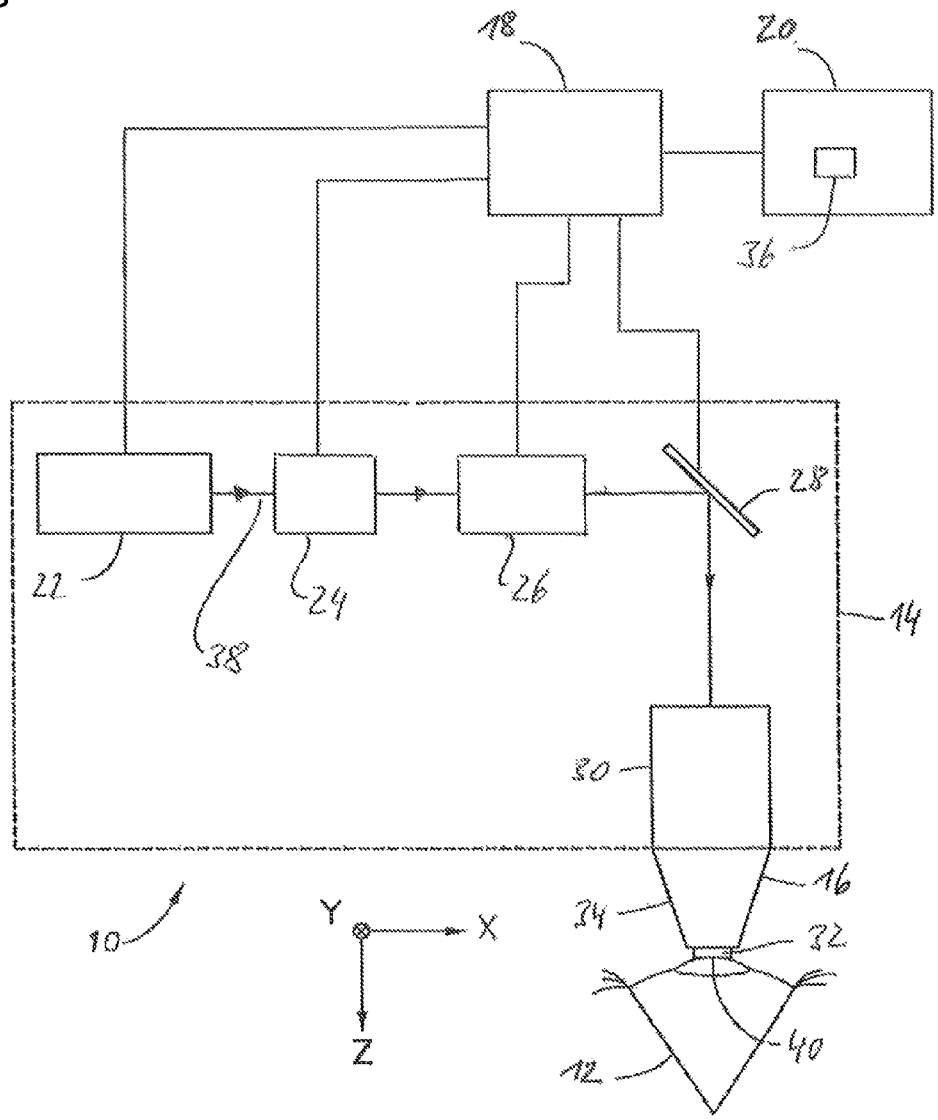
FIG. 1 illustrates an example of a laser apparatus for creating incisions in a human eye according to an embodiment.

Referring now to the drawings, example embodiments of the disclosed apparatus and method are shown in detail. The following description is in no way intended to be exhaustive or to otherwise limit or restrict the accompanying claims to the specific embodiments shown in the drawings and disclosed herein. Although the drawings represent possible embodiments, the drawings are not necessarily to scale and certain features may be simplified, exaggerated, removed, or partially sectioned to better illustrate the embodiments. In addition, certain drawings may be in schematic form.

FIG. 1 illustrates an example embodiment of an apparatus 10 configured to create incisions in human eye tissue. In the illustrated embodiment, the apparatus 10 includes a laser device and a control computer. The laser device can create incisions in a cornea, a human lens, or another structure of a human eye using ultrashort-pulsed laser radiation. As used herein, ultrashort is intended to mean a pulse duration within the picosecond or femtosecond or attosecond range.

In the illustrated example of FIG. 1, the apparatus 10 performs laser surgery on a human eye 12. The apparatus 10 includes a laser device 14, a patient adapter 16, a control computer 18, and a memory 20, which may be coupled as shown. The laser device 14 includes a laser source 22, a pulse train shaping device 24, a scanner 26, one or more optical mirrors 28, and a focusing objective 30, which may be coupled as shown. The patient adapter 16 includes a contact element 32 and a support sleeve 34. The memory 20 stores a control program 36.

The laser source 22 generates a laser beam 38 with ultrashort pulses. The focal point of the laser beam 38 may create a laser-induced optical breakdown (LIOB) in tissues such as the cornea or another structure of the eye 12. The laser beam 38 may have any suitable wavelength, such as a wavelength in the range of 300-1900 nanometers (nm), for example a wavelength in the range of 300-650, 650-1050, 1050-1250, 1100-1400 or 1400-1500 or 1500-1900 nm. The laser beam 38 may also have a relatively small focus volume, e.g. 5 micrometers ($\mu$m) or less in diameter.

The pulse train shaping device 24, scanner 26, optical mirrors 28, and focusing objective 30 are in the beam path of the laser beam 38. The laser source 22 generates the laser beam 38 as a sequence of laser radiation pulses which follow one another at regular intervals. The pulse train shaping device 24 forms the sequence provided by the laser source 22 into a pulse train composed of successive pulse groups (or "bursts"). Each pulse group of the pulse train comprises a plurality of radiation pulses. In certain embodiments, the pulses of a pulse group are formed by selection of directly successive pulses of the sequence provided by the laser source 22, so that the time interval between the pulses of the group corresponds to the time interval between the pulses of the sequence provided by the laser source 22. In other embodiments, the time interval between the pulses of a pulse group may be larger than the time interval between the pulses of the sequence provided by the laser source 22. For this, the pulse train shaping device 24 may select for a pulse group, pulses of the sequence which are separated by at least one intervening pulse. By contrast, the time interval between successive pulse groups of the pulse train output by the pulse train shaping device 24 is a multiple of the time interval between the pulses of a group. The pulse train shaping device 24 may additionally provide an amplification function for the pulses of the pulse train.

The scanner 26 is configured to transversely and longitudinally control the focal point of the laser beam 38. "Transverse" refers to a direction at right angles to the direction of propagation of the laser beam 38, and "longitudinal" refers to the direction of beam propagation. The transverse plane may be designated as an x-y plane, and the longitudinal direction may be designated as the z-direction.

The scanner 26 may transversely direct the laser beam 38 in any suitable manner. For example, the scanner 26 may include a pair of galvanometrically actuated scanner mirrors that can be tilted about mutually perpendicular axes. As another example, the scanner 26 may include an electro-optical crystal that can electro-optically steer the laser beam 38. The scanner 26 may longitudinally direct the laser beam 38 in any suitable manner. For example, the scanner 26 may include a longitudinally adjustable lens, a lens of variable refractive power, or a deformable mirror that can control the z-position of the beam focus. The focus control components of the scanner 26 may be arranged in any suitable manner along the beam path, e.g., in the same or different modular units.

The one or more optical mirrors 28 direct the laser beam 38 towards the focusing objective 30. For example, an optical mirror 28 may be an immovable deviating mirror or a movable deviating mirror. As an alternative, an optical element that can refract and/or diffract the laser beam 38 may be provided in place of an optical mirror 28.

The focusing objective 30 focuses the laser beam 38 onto a target area of the eye 12. The focusing objective 30 may be separably coupled to the patient adapter 16. The focusing objective 30 may be any suitable optical device, such as an F-Theta objective.

The patient adapter 16 interfaces with the cornea of the eye 12. The sleeve 34 couples to the focusing objective 30 and retains the contact element 32. The contact element 32 is transparent or translucent to the laser radiation and has an abutment face 40 that interfaces with the cornea and may level a portion of the cornea. In certain embodiments, the abutment face 38 is planar and forms a planar area on the cornea. The abutment face 40 may be on an x-y plane, so that the planar area is also on an x-y plane. In other embodiments, the abutment face 40 need not be planar, e.g., may be convex or concave.

The control computer 18 controls controllable components of the laser device 14 such as, e.g., the laser source 22, pulse train shaping device 24, scanner 26 and/or mirror(s) 28, in accordance with the control program 36. The control program 36 contains computer code that instructs the controllable components to focus the pulsed laser radiation at a region of the eye 12 to photodisrupt at least a portion of the region.

The scanner 26 may direct the laser beam 38 to form incisions of any suitable geometry. Any suitable portion of the tissue of the eye 12 may be photodisrupted. The apparatus 10 may photodisrupt a tissue layer by moving the focus of the laser beam 38 along a given scan path. As the laser beam 38 travels along the scan path, the radiation pulses create photodisruptions in the tissue of the eye 12. More specifically, a photodisruption is caused by each pulse group of the pulse train output by the pulse train shaping device 24. By juxtaposition of a plurality of photodisruptions, an incision of any desired geometry can be created in the eye 12.

Figure 2:
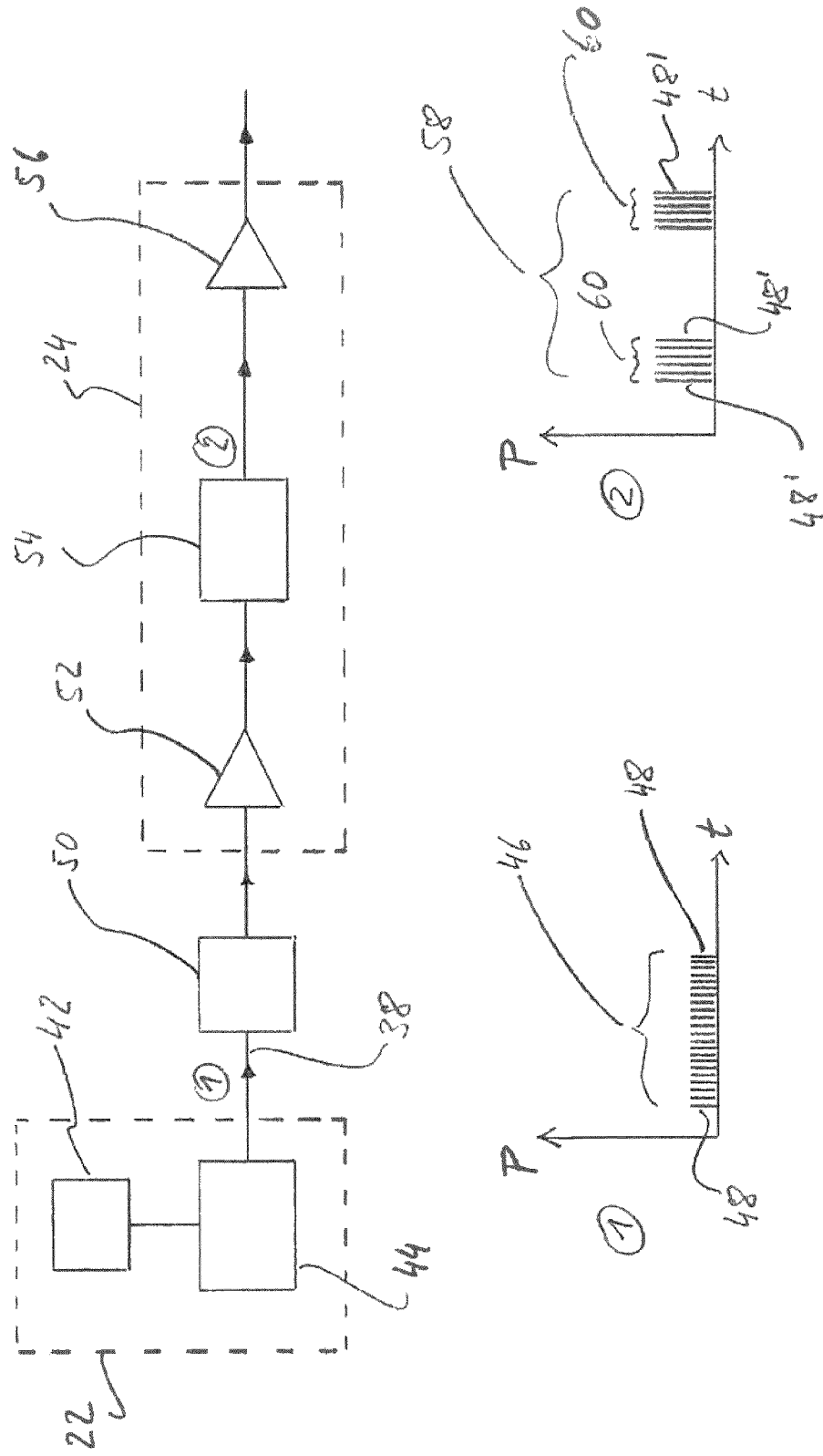
FIG. 2 illustrates in greater detail components of a laser device of the apparatus of FIG. 1 according to an embodiment.

Reference is now made additionally to FIG. 2. In this Figure, the laser source 22 is shown as including a pump source 42 and a laser resonator 44. The pump source 42 may be configured for electrical or optical pumping of the laser resonator 44. For example, the pump source 42 may include an electronic semiconductor drive circuit or a pump diode. The laser resonator 44 may be of the VECSEL type. VECSEL stands for Vertical External-Cavity Surface-Emitting Laser and designates a type of semiconductor laser which is based on a surface-emitting semiconductor gain chip and a resonator which is completed with one or several external optical elements. More detailed background information on VECSEL-type lasers can be found in *Semiconductor Disc Lasers: Physics and Technology*, edited by Oleg G. Okhotnikov, Wiley-VCH Verlag GmbH & Co. KGaA, Print ISBN: 978-3-527-40933-4, the content of which is incorporated herein by reference. In other embodiments, the laser resonator 44 is another type of semiconductor laser such as, e.g., a VCSEL or MIXSEL. For passive mode locking, the resonator 44 may include a saturable absorber mirror (SAM) made in semiconductor technology.

The laser source 22 generates the laser beam 38 as a sequence of ultrashort radiation pulses following each other at regular intervals and having a pulse repetition rate of at least 100 MHz. A P-t diagram in the lower left portion of FIG. 2 illustrates schematically the pulse sequence at a position (1) at the output of the laser source 22. The sequence is denoted 46 and individual pulses of the sequence are denoted 48. In the P-t diagram, P designates power and t designates time. The pulse repetition rate of the pulses 48 of the sequence 46 may have any suitable value in the range 100 MHz-500 MHz, 500 MHz-1 GHz, 1 GHz-2 GHz, 2 GHz-5 GHz, 5 GHz-10 GHz, or 10 GHz-20 GHz. The pulse energy (and likewise the pulse peak power) is the same (within applicable tolerances as are inevitable in the creation of ultrashort laser pulses) for all pulses 48 of the sequence 46. The pulse energy may have any suitable value and may, for example, be in the picojoule (pJ) range. For example, the pulse energy of the pulses 48 output by the laser source 22 may be at least about 1 pJ and at most about 10 nJ per pulse. In certain embodiments, the pulses 48 may have a pulse energy in the range 1-100 pJ, 100-500 pJ, 0.5-1 nJ, or 1-10 nJ.

In the illustrated embodiment of FIG. 2, an optical isolator 50 is coupled between the laser source 22 and pulse train shaping device 24 to suppress back reflection of pulses into the laser resonator 44. Suitable structures of optical isolators for the intended purpose are conventionally known, and a detailed discussion thereof will be omitted herein.

After passing through the optical isolator 50, the laser beam 38 enters the pulse train shaping device 24. The pulse train shaping device 24 includes a pre-amplifier 52, a pulse selector 54 and a post-amplifier (or "booster amplifier") 56. The pre-amplifier 52 effects an amplification of the pulses 48 of the sequence 46 by any suitable factor. For example, the amplification factor can be in the range $10^2$-$10^4$, 200-5000, 500-3000, or 700-2000. In certain embodiments, the pre-amplifier 52 effects an amplification of the pulses 48 to an energy level in the nanojoule (nJ) range, e.g., the single-digit or double-digit nJ-range. In certain embodiments, the pre-amplifier 52 is a semiconductor optical amplifier (SOA). In other embodiments, the pre-amplifier 52 is a fiber amplifier.

The pulse selector 54 performs pulse picking on the (pre-amplified) pulses 48 of the continuous pulse sequence 46 to generate a pulse train consisting of successive pulse groups each comprising a plurality of (pre-amplified) pulses. A P-t diagram in the bottom right of FIG. 2 illustrates schematically a pattern of the pulse train output by the pulse selector 54, i.e. at a position (2) along the beam path of the laser beam 38. The pulse train is designated 58, and groups (or "bursts") of pulses in the train are designated 60. The pulse groups 60 each include the same number of (pre-amplified) pulses. The pre-amplified pulses are designated 48'. The number of pulses 48' in each pulse group 60 may have any suitable value, for example, may be in the range 10-1000, 10-500, 20-200, or 50-150. The pulse energy is the same for all pulses 48' in a pulse group 60.

The pulse selector may be any suitable device allowing to select individual pulses or pulse groups from the continuous pulse sequence 46 and pass the selected pulses or pulse groups on to the post-amplifier 56. For example, the pulse selector 54 may be implemented as an accousto-optical modulator (AOM). Other embodiments of a pulse selected may include an electro-optical modulator or a Pockels cell. The repetition rate of the pulse groups 60 is smaller by at least an order 2 or 3 than the pulse repetition rate of the sequence 46. The repetition rate of the pulse groups 60 is not higher than about 1 MHz and ranges, for example, from 100 to 500 kHz or 500 kHz to 1 MHz.

The pulse repetition rate of the pulses 48' in a pulse group 60 is the same as the repetition rate of the pulses 48 of the sequence 46. Defining the ratio of the duration of a group 60 to the repetition interval of the groups 60 as a duty cycle, the value of the duty cycle may be in the range 2-30, 5-20, or 5-15%. For example, the duty cycle may be about 10%.

The post-amplifier 56 performs amplification of the pulses 48' of the pulse train 60 to raise the energy level of the pulses 48' by a factor which is at least 10, 20, 50 or 100. In certain embodiments, the post-amplifier 56 amplifies the pulses 48' to an energy level in the 1-digit, 2-digit or 3-digit nJ-range or the 1-digit or 2-digit microjoule (μJ) range. For example, the post-amplifier amplifies the pulses 48' to about a value of 1 μJ. The post-amplifier may include a fiber amplifier, for example, a largemode area (LMA) fiber amplifier or a large pitch fiber (LPF).

Referring back to FIG. 1, the patient adapter 16 with its contact element 32 provides an exit location at which the laser beam 38 is output from the apparatus 10 toward the target (i.e. the eye 12). As output via the patient adapter 16, the pulses of a pulse group have the same energy and power and each individual pulse of a pulse group of the laser beam 38 has insufficient energy to achieve a laser-induced optical breakdown in the eye tissue under treatment. In other words, the energy of each individual pulse is below an applicable energy threshold for single-pulse applications, i.e. smaller than an energy level needed to induce a LIOB by a single pulse. Yet the aggregate effect of the entirety of the pulses of a pulse group output at the patient adapter 16 is sufficient to cause a LIOB in the treated tissue. In certain embodiments, the scanner 26 is controlled to move the laser beam 38 continuously, so that the pulses of a pulse group are applied to the treated eye tissue "on-the-fly", i.e. without stopping the movement of the laser beam 38. As the temporal displacement of the pulses of a pulse group is sufficiently short in consideration of the scanning velocity of the laser beam 38, it is nevertheless insured that the pulses of a pulse group are fired at the eye tissue with sufficient positional overlap to achieve the desired LIOB. At the same time, the temporal offset of successive groups of the pulse train 60 is sufficiently large to ensure that successive groups are fired at spaced locations of the eye tissue without substantial overlap. In this way, the series of pulse groups in the pulse train 60 are effective to cause a series of photodisruptions in the tissue of the eye 12.

Although not shown in the drawings, the laser device 14 may include in certain embodiments additional optical components such as a pulse stretcher, a pulse compressor, a reflection grating, and/or a transmission grating. These components are conventional per se, so that a detailed description thereof may be omitted herein.

Figure 3:
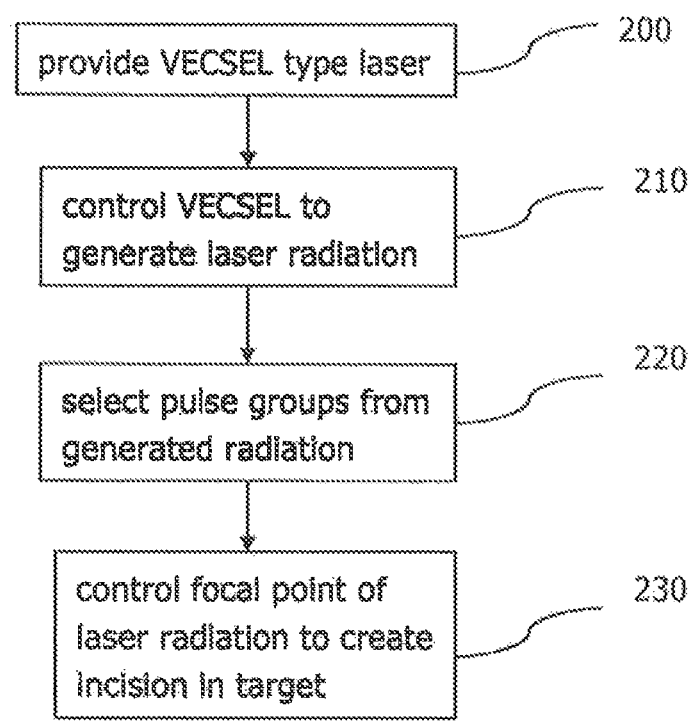
FIG. 3 illustrates an example of a method for creating incisions in a human eye according to an embodiment.

FIG. 3 is an example of a method for creating an incision in a target, for example, in the eye 12. The method may be performed using the apparatus 10. At step 200, a VECSEL-type laser may be provided. At step 210, the VECSEL-type laser may be controlled to generate laser radiation. The generated radiation may have a pulse repetition rate of about 1 GHz or more. At step 220, pulse groups may be selected from the generated radiation, wherein the pulse groups may have a repetition rate of about 1 MHz or less. At step 230, a focal point of the laser radiation may be controlled to move over a target area of a target to create an incision in the target. The incision may have any suitable geometry and may be created, for example, in the cornea or the lens of a human eye 12.

The invention claimed is:

1. A laser apparatus comprising:
   a semiconductor laser source configured to generate pulsed laser radiation having an ultrashort pulse duration in the femtosecond range or shorter and having a pulse repetition rate of at least 100 MHz;
   a selector configured to select groups of pulses from the laser radiation, each pulse group comprising a plurality of pulses at a pulse repetition rate of at least 100 MHz, wherein the pulse groups have a group repetition rate of no more than 1 MHz and are time-displaced by at least 500 ns;
   a scanner device configured to scan a focal point of the pulsed laser radiation;
   a controller configured to control the scanner device based on a control program including instructions that, when executed by the controller, bring about the creation of a LIOB-based photodisruption in human eye tissue for each pulse group.

2. The laser apparatus of claim 1, wherein the laser source includes a semiconductor laser.

3. The laser apparatus of claim 2, wherein the semiconductor laser is one of a VECSEL type, VCSEL type and MIXSEL type.

4. The laser apparatus of claim 1, wherein the pulse repetition rate is at least 500 MHz, 800 MHz or 1 GHz.

5. The laser apparatus of claim 1, wherein a pulse group includes no less than 10 pulses or 20 pulses or 50 pulses or 80 pulses or 100 pulses.

6. The laser apparatus of claim 1, wherein a pulse group has a group duration of no more than 200 ns or 150 ns or 120 ns.

7. The laser apparatus of claim 1, wherein successive pulse groups are time-displaced by at least the duration of a pulse group.

8. The laser apparatus of claim 1, comprising an exit location for outputting the pulsed laser radiation towards a target material, wherein pulses output at the exit location are characterized by pulse characteristics ensuring the generation of a laser-induced optical breakdown in human eye tissue by each pulse group.

9. The laser apparatus of claim 8, wherein the aggregate energy of a group of pulses output at the exit location is in the range of nanojoules or microjoules.

10. The laser apparatus of claim 9, wherein the aggregate energy of a group of pulses output at the exit location is between 0.1 and 1 microjoules.

11. The laser apparatus of claim 8, wherein the energy of a pulse output at the exit location is in the range of picojoules or nanojoules.

12. The laser apparatus of claim 1, wherein a pulse group has the same energy for all pulses of the group.

13. The laser apparatus of claim 1, wherein a pulse group has the same peak power for all pulses of the group.

14. The laser apparatus of claim 1, comprising a first amplifier configured to amplify the pulses of the pulsed laser radiation prior to the selection of the pulse groups.

15. The laser apparatus of claim 14, wherein the first amplifier is configured to amplify the energy of a pulse from picojoules to nanojoules.

16. The laser apparatus of claim 14, comprising a second amplifier configured to amplify the pulses selected by the selector.

* * * * *